United States Patent [19]
Dorigotti et al.

[11] 4,086,343
[45] Apr. 25, 1978

[54] ACYLATED HYDRAZINOPYRIDAZINE ANTIHYPERTENSIVES

[75] Inventors: Luciano Dorigotti; Francesco Parravicini, both of Milan, Italy

[73] Assignee: I.S.F. SpA, Milan, Italy

[21] Appl. No.: 804,272

[22] Filed: Jun. 7, 1977

[30] Foreign Application Priority Data

Jun. 11, 1976 Italy ................................. 24177/76

[51] Int. Cl.² .................... C07D 237/20; A61K 31/50
[52] U.S. Cl. ................................ 424/250; 260/250 A
[58] Field of Search .................... 260/250 A, 424, 250

[56] References Cited
U.S. PATENT DOCUMENTS

| 3,535,317 | 10/1970 | Bellasio | 260/250 A |
| 3,769,278 | 10/1973 | Pifferi | 260/250 A |
| 3,925,381 | 12/1975 | Carpi et al. | 260/250 A |
| 4,002,753 | 1/1977 | Carpi et al. | 260/250 A |

Primary Examiner—Donald G. Daus
Assistant Examiner—Mark L. Berch
Attorney, Agent, or Firm—Stevens, Davis, Miller & Mosher

[57] ABSTRACT

Antihypertensive compounds comprising hydrazinopyridazine derivatives of the formula:

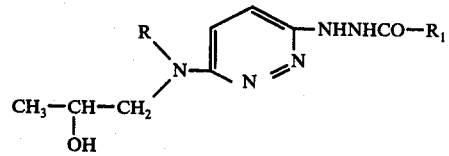

wherein R is an alkyl radical containing from 1 to 4 carbon atoms or an alkyl radical having from 1 to 4 carbon atoms substituted with a hydroxy group and $R_1$ is a hydrogen atom, an alkyl radical containing from 1 to 4 carbon atoms, a phenyl or 3-pyridyl group and their non-toxic pharmaceutically acceptable salts with inorganic or organic acids. Also pharmaceutical compositions containing the same.

10 Claims, No Drawings

ACYLATED HYDRAZINOPYRIDAZINE ANTIHYPERTENSIVES

The present invention relates to hydrazinopyridazine derivatives having antihypertensive activity and pharmaceutical compositions containing the same.

More particularly, the new compounds of the invention are 6-(2'-acylhydrazino)pyridazines substituted in position 3 with the group N(2'-hydroxypropyl)amino and having the general formula:

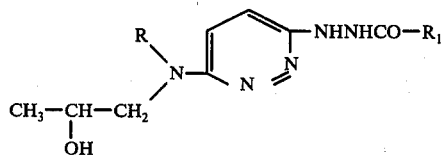

wherein R is an alkyl radical containing from 1 to 4 carbon atoms optionally substituted with a hydroxy group and $R_1$ is a hydrogen atom or an alkyl radical containing from 1 to 4 carbon atoms, a phenyl or 3-pyridyl group. The present invention also relates to the pharmaceutically acceptable non-toxic salts of the compounds of Formula I with suitable inorganic or organic acids.

The term alkyl radical containing from 1 to 4 carbon atoms comprises linear or branched saturated alkyl radicals, and more particularly methyl, ethyl, propyl, butyl, isobutyl, t. butyl, 2-hydroxyethyl and 2-hydroxypropyl.

The term inorganic acid comprises among others, hydrochloric, hydrobromic, sulphuric and phosphoric acid. The term organic acid comprises among others, acetic, succinic, benzoic and p-toluenesulphonic acid.

Among the known hydrazinopyridazines having antihypertensive activity, the 3-(2'-hydroxypropyl)alkylamino-6-hydrazinopyridazines described and claimed in U.S. Pat. No. 3,769,278 are particularly interesting. Compared to such compounds which structurally are those known to be most similar to the compounds of the present invention, the compounds of Formula I have been found to be practically free from tachycardizing activity and to produce an antihypertensive effect which takes place with slow progression and more long-lasting results. The activity of compounds of Formula I was tested in the renal hypertensive awake rate according to the A. Grollman method (Proc. Soc. Exptl. Biol. and Med., 57,102,1944) using oral administration. The products were administered to groups of four animals each, at no less than three dosage levels, according to the compound activity. These dosage levels were for Hydralizine: 4,8 and 16 mg/kg; for 3-(2'hydroxypropyl)methylamino-6-hydrazinopyridazine: 1,2 and 4 mg/kg and for 1,3-(2'-hydroxypropyl)methylamino-6-(2'-acetylhydrazino)pyridazine: 2,4 and 8 mg/kg. The arterial pressure (press. and the heart frequency (freq.) were measured immediately before and 1,3,5,7,24 and 30 hours after administration. The results of the experiments carried out with a compound exemplifying the class of Formula I, 3-(2'-hydroxypropyl)-methylamino-6-(2'-acetylhydrazino)pyridazine compared to hydralazine and 3-(2'-hydroxypropyl)methylamino-6-hydrazinopyridazine are reported in the following Table.

TABLE

| Compound | Heart Freq. $DE_{25}$ mg/kg | Press. $DE_{25}$ mg/kg | Half effect time (in hrs) |
|---|---|---|---|
| Hydralazine | 8.0 | 8.1 | 5 |
| 3-(2'-hydroxypropyl) methylamino-6-hydrazinopyridazine | 2.0 | 1.7 | 5 |
| 3-(2'hydroxypropyl) methylamino-6-(2'-acetyl-hydrazino)pyridazine | 6 | 2 | >30 |

$DE_{25}$ indicates the dose which causes a fail in pressure (Press.$DE_{25}$) or an increase in the heart frequency (Freq. $DE_{25}$) of the 25 percent compared to the basal value. These values have been determined at the peak-effect. Half effect time means the interval of time elapsing between the treatment and the moment at which the pressure fall is reduced to one half compared to the maximum effect.

From the values reported in Table I it is evident that the product of the invention, although it exhibits antihypertensive activity of an intensity equivalent to that of 3-(2'-hydroxypropyl) methylamino-6-hydrazinopyridazine, has a considerably longer duration of action (6 times longer) and moreover, at clearly antihypertensive doses, is to be considered free from tachycardizing activity. That is clearly pointed out by the value of the ratios freq. $DE_{25}$/press. $DE_{25}$ reported hereinafter.

TABLE II

| Compound | Freq. $DE_{25}$/Press. $DE_{25}$ |
|---|---|
| Hydralazine | 0.98 |
| 3-(2'-hydroxypropyl) methylamino-6-hydrazinopyridazine | 1.17 |
| 3-(2'-hydroxypropyl) methylamino-6-(2'-acetylhydrazino) pyridazine | 3 |

The absence of tachycardizing activity at the therapeutic doses indicates that the compounds of the invention can be usefully applied in all cases of hypertension, but especially in cases of hypertension where heart failures are present.

The compounds of Formula I can be prepared starting from 3-(2'-hydroxypropyl)-alkylamino-6-hydrazinopyridazines prepared according to the process described in U.S. Pat. No. 3,769,278 by means of acylation under anhydrous conditions in a suitable solvent at a temperature between −10° and 10° C. An organic base, preferably pyridine, is usefully used as the solvent. Acylation is carried out in the presence of an excess of the acylating agent generally consisting of the chloride or the anhydride of the desired acid. The starting substances are preferably used in the form of salts and the final products I, as free bases, are obtained from the corresponding compounds salified according to known techniques.

The following Examples are given for the purpose of illustrating the present invention without limiting it.

EXAMPLE 1

3-(2'-Hydroxypropyl)methylamino-6-(2'-acetylhydrazino)pyridazine

To a solution of 27g of 3-(2'-hydroxypropyl)methylamino-6-hydrazinopyridazine dihydrochloride in 200 ml of anhydrous pyridine, 7 ml of acetyl chloride are slowly added dropwise at 0° C. When addition is completed, the reaction mixture is left to stand under stirring for two hours at 0°–5° C and then overnight at 0° C. The pyridine is removed by distillation in the rotating evaporator under vacuum at approximately 10° C and an oily residue is obtained which is treated at 0° C and under stirring with a solution of sodium methylate. The product obtained is dried at 10° C, the residue taken up with isopropyl alcohol, filtered on cellite cake and the filtrate, dried under vacuum, gives 3-(2'-hydroxypropyl) methylamino-6-(2'-acetylhydrazino)-pyridazine which, recrystallized from ethyl alcohol, melts at 168° C.

EXAMPLE 2

3-(2'-Hydroxypropyl)ethylamino-6-(2'-acetylhydrazino)pyridazine

Following the procedures described above, but using as the starting substance 3-(2'-hydroxypropyl)ethylamino-6-hydrazinopyridazine dihydrochloride, there is obtained 3-(2'-hydroxypropyl)-ethylamino-6-(2'-acetylhydrazino)pyridazine melting at 156°–158° C.

EXAMPLE 3

3-(2'-Hydroxypropyl)methylamino-6-(2'-propionylhydrazino)pyridazine

Following the procedure described in Example 1, but using as the acylating agent propionyl chloride, there is obtained 3-(2'-hydroxypropyl)methylamino-6-(2'-propionylhydrazino)pyridazine melting at 155°–157° C.

EXAMPLE 4

3-[bis-(2'-hydroxypropyl)amino]-6-(2'-acetylhydrazino)pyridazine

Following the procedure described in Example 1, but using as the starting substance 3-[bis-(2'-hydroxypropyl)-amino]-6-hydrazinopyridazine, there is obtained 3-[bis-(2'-hydroxypropyl) amino]-6-(2'-acetylhydrazino)pyridazine melting at 150°–155° C.

EXAMPLE 5

3-(2'-Hydroxypropyl)methylamino-6-(2'-pivaloylhydrazino)pyridazine

Following the procedure described in Example 1, but using as the acylating agent pivaloyl chloride, there is obtained 3-(2'-hydroxypropyl)methylamino-6-(2'-pivaloylhydrazino)pyridazine melting at 170°–172° C.

EXAMPLE 6

3-(2'-Hydroxypropyl)methylamino-6-(2'-nicotinoylhydrazino)pyridazine

Following the procedure described in Example 1, but using as the acylating agent nicotinoyl chloride, there is obtained 3-(2'-hydroxypropyl)methylamino-6-(2'-nicotinoylhydrazino)pyridazine melting at 75° C (with decomposition).

EXAMPLE 7

3-(2'-Hydroxypropyl)methylamino-6-(2'-formylhydrazino)pyridazine

Thirteen and one half grams of 3-(2'-hydroxypropyl)-methylamino-6-hydrazinopyridazine dihydrochloride are dissolved in 25 ml of formic acid, and there are subsequently added thereto at 0° C 6 ml of acetic anhydride and after 30 minutes 8.4 g sodium bicarbonate. The mixture is stirred at 0° C for 30 minutes and left at room temperature overnight. The solvent is removed and the residue consisting of 3-(2'-hydroxypropyl)methylamino-6-(2'-formylhydrazino)pyridazine is recrystallized from acetone/ethanol (8:2). It melts at 130°–132° C.

The compounds of the invention are suitable for the oral and parenteral administration, with particular preference for the oral administration. According to the invention the new composition having antihypertensive activity contains as active ingredients the new compounds of formula I in admixture with an inert pharmaceutical carrier which may be solid or liquid and is selected among those usually employed in the pharmaceutical technique for the preparation of compositions suitable for oral or parenteral administration. In accordance to the carrier the compositions may be solid or liquid. The compositions object of the invention comprise a compound of formula I in such an amount so that the desired therapeutic effect be obtained. The daily dosage for human treatment of the compounds of formula I to provoke the desired antihypertensive effect is generally comprised between 2 mg and 150 mg.

What is claimed is:

1. A hydrazinopyridazine compound of the formula:

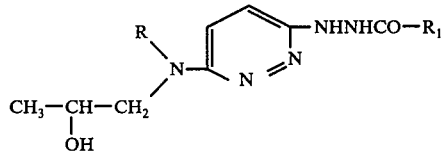

wherein R is an alkyl radical containing from 1 to 4 carbon atoms or an alkyl radical having from 1 to 4 carbon atoms substituted iwith a hydroxy group and $R_1$ is a hydrogen atom, an alkyl radical containing from 1 to 4 carbon atoms, a phenyl or 3-pyridyl group and their non-toxic pharmaceutically acceptable salts with inorganic or organic acids.

2. A compound according to claim 1 which is 3-(2'-hydroxypropyl)methylamino-6-(2'-acetylhydrazino)-pyridazine.

3. A compound according to claim 1 which is 3-(2'-hydroxypropyl)ethylamino-6-(2'-acetylhydrazino)-pyridazine.

4. A compound according to claim 1 which is 3-(2'-hydroxypropyl)methylamino-6-(2'-propionylhydrazino)pyridazine.

5. A compound according to claim 1 which is 3-[bis-(2'-hydroxypropyl)amino]-6-(2'-acetylhydrazino)-pyridazine.

6. A compound according to claim 1 which is 3-(2'-hydroxypropyl)methylamino-6-(2'-pivaloylhydrazino)-pyridazine.

7. A compound according to claim 1 which is 3-(2'-hydroxypropyl)methylamino-6-(2'-nicotinoylhydrazino)pyridazine.

8. A compound according to claim 1 which is 3-(2'-hydroxypropyl)methylamino-6-(2'-formylhydrazino)-pyridazine.

9. A pharmaceutical composition comprising an antihypertensively effective amount of a compound according to claim 1 and a pharmaceutically acceptable carrier.

10. A pharmaceutical composition comprising an antihypertensively effective amount of a compound according to claim 2 and a pharmaceutically acceptable carrier.

* * * * *

UNITED STATES PATENT OFFICE
CERTIFICATE OF CORRECTION

Patent No. 4,086,343          Dated April 25, 1978

Inventor(s)   Luciano DORIGOTTI and Francesco PARRAVICINI

It is certified that error appears in the above-identified patent and that said Letters Patent are hereby corrected as shown below:

Column 1, line 51, change "rate" to -- rat --.

Column 1, line 56, change "Hydralizine" to --Hydralazine--.

Column 1, line 58, change "1,3-(2'-hydroxypropyl)" to -- 3-(2'-hydroxypropyl) --.

Column 1, line 60, change "(press." to -- (press.) --.

Column 4, line 34, change "substituted iwith" to -- substituted with --.

Signed and Sealed this

Nineteenth Day of September 1978

[SEAL]

Attest:

RUTH C. MASON
*Attesting Officer*

DONALD W. BANNER
*Commissioner of Patents and Trademarks*